Miyazawa

[11] 4,283,145
[45] Aug. 11, 1981

[54] OPTICAL SYSTEM FOR THE DETECTION OF FLAWS IN BOTTLES OR THE LIKE

[75] Inventor: Takashi Miyazawa, Funabashi, Japan
[73] Assignee: Kirin Beer Kabushiki Kaisha, Tokyo, Japan
[21] Appl. No.: 11,813
[22] Filed: Feb. 13, 1979
[51] Int. Cl.³ .............................................. G01N 21/01
[52] U.S. Cl. ..................................... 356/364; 250/224; 350/6.6; 356/237; 356/240
[58] Field of Search ..................... 356/237–240, 356/364, 369, 236, 446, 215; 250/223 B, 224; 350/6.3, 6.5, 6.6, 6.7, 6.1, 6.8, 6.9

[56] References Cited
U.S. PATENT DOCUMENTS

| | | | |
|---|---|---|---|
| 2,265,037 | 9/1939 | Gulliksen | 356/240 |
| 2,930,898 | 3/1960 | Nuttall et al. | 250/223 B |
| 2,984,747 | 5/1961 | Walker | 356/215 |
| 3,437,393 | 4/1969 | Baker et al. | 350/6.6 |
| 3,717,772 | 2/1973 | Engman | 350/6.6 X |
| 3,770,969 | 11/1973 | Ansevin et al. | 356/240 |

FOREIGN PATENT DOCUMENTS

| | | | |
|---|---|---|---|
| 46-14085 | 4/1971 | Japan | 350/6.3 |
| 526810 | 8/1976 | U.S.S.R. | 356/442 |

OTHER PUBLICATIONS

Hauge, P. S., "Method of Characterizing Optical Systems That Depolarized Light", IBM Tech. Disclosure Bulletin, vol. 20, No. 3, (Aug. 1977).

Primary Examiner—John K. Corbin
Assistant Examiner—Bruce Y. Arnold
Attorney, Agent, or Firm—Ladas & Parry

[57] ABSTRACT

In order to enable a laser beam to scan the complete inside surfaces of an empty bottle or the like, two mirrors oscillating about right angular axes are employed which successively reflect the laser beam. The oscillations of the two mirrors are correlated to impart an annular or spiral scanning motion to the laser beam. Subsequently passing through a converging lens, which is focused at the mouth of the bottle being tested, the laser beam enters the bottle for point-by-point scanning of its surfaces. The presence of a flaw in the bottle is sensed from the intensity of the laser beam that has penetrated, or has been reflected from, the bottle, as by an integrating sphere and a photoelectric detector mounted in position thereon. Various other embodiments of the invention and modifications are disclosed.

10 Claims, 15 Drawing Figures

OPTICAL SYSTEM FOR THE DETECTION OF FLAWS IN BOTTLES OR THE LIKE

BACKGROUND OF THE INVENTION

1. Field of the Invention

This invention relates to a system for optically detecting flaws in bottles, cups, bowls, cans, and various other containers or like articles. A more specific aspect of the invention concerns such a system for automatically detecting flaws in used and cleaned bottles for beverages or liquors, prior to the refilling of such bottles. By the term "flaws" are meant cracks, breaches, fissures, scratches, adhering foreign matter, and any other imperfections detectable by the system of this invention.

2. Description of the Prior Art

Bottles for some beverages or liquors are recycled; that is, they are recovered from the consumers, cleaned, and put to reuse. Bottle cleaning machines in current use are such, however, that they may not necessarily make the bottles free of all foreign matter firmly sticking thereto. Further, some bottles may have cracks and similar defects formed therein. All such faulty bottles must be discriminated from flawless ones before they are refilled, and should not be reused from the standpoint of hygiene or of the forestallment of actual or potential danger.

According to a typical conventional apparatus for the detection of bottle flaws, a light source underlying a bottle to be tested irradiates the complete surface of its bottom. Disposed at the mouth of the bottle, a photodetector senses the presence of a flaw, if any, in the bottle from the intensity of the incident light that has passed through its bottom.

An objection to this prior art apparatus is its comparatively poor ability of detecting localized flaws and those lying adjacent to the bottom perimeter or on the side wall of the bottle. This drawback arises principally from the application of light only to the bottom of the bottle and from the insufficient intensity of the light. Additionally, since the light falls on the bottle at one time, the photodetector is required to sense its possible flaw from a small change in the incident radiation.

Another objection to the prior art apparatus is its inability, or at least very poor ability, to detect such transparent foreign matter as cellophane adhering to a bottle. This is an inevitable result of its operating principle of sensing flaws in a bottle from the intensity of the light that has penetrated its bottom.

SUMMARY OF THE INVENTION

It is an object of this invention to provide an improved system for accurately detecting all sorts of possible flaws in bottles and other articles.

Another object of the invention is to provide such a system capable of detecting flaws lying not only at the bottom but also on the side wall of a bottle or the like.

A further object of the invention is to provide such a system which correctly responds even to transparent foreign matter sticking to a bottle or the like in any position thereon.

A still further object of the invention is to provide such a flaw detecting system which works even under bright ambient light without loss or diminution of the above noted advantages.

Stated in brief, this invention provides a flaw detecting system comprising means for generating a light beam, means disposed in the path of the light beam for imparting an annular or spiral scanning motion thereto, such that the light beam is enabled to scan all surfaces of an article being held in a preassigned position to be tested as to the presence or absence of a flaw, and means for receiving the light beam that has scanned the article and for sensing a flaw, if any, in the article from the intensity of the incident light.

The flaw detecting system usually employs a laser, such as a gas laser, as the light source. Various means can be employed to cause the annular or spiral scanning motion of the laser beam. According to an example of such various possible means disclosed herein, two mirrors capable of successively reflecting the laser beam are arranged for correlated oscillation about respective axes at right angles to each other.

If the article being tested is a beer bottle, for example, with its constricted mouth, then a converging lens may be disposed between the oscillatory mirror system and the bottle lying in the preassigned position. Focused at the mouth of the bottle, the converging lens serves to direct the laser beam into the bottle so as to enable the beam to scan the bottom as well as the side wall of the bottle point by point.

A variety of means can also be employed for receiving the laser beam that has scanned the bottle and for sensing therefrom a possible flaw in the bottle. One example includes an integrating sphere arranged to receive the laser beam that has passed through the bottle, and a photodetector mounted in the window of the integrating sphere so as to be irradiated by the light reflected from its inside surface. Any flaw in the bottle manifests itself as a change in the electrical output of the photodetector. Thus, with its point-by-point scanning principle, the invention enables the detection of a flaw in a bottle or the like with great accuracy.

The above and other objects, features and advantages of this invention and the manner of attaining them will become more readily apparent, and the invention itself will best be understood, from the following description and appended claims, with reference to the accompanying drawings showing several preferred embodiments of the invention.

DESCRIPTION OF THE PREFERRED EMBODIMENTS

Figure 1:
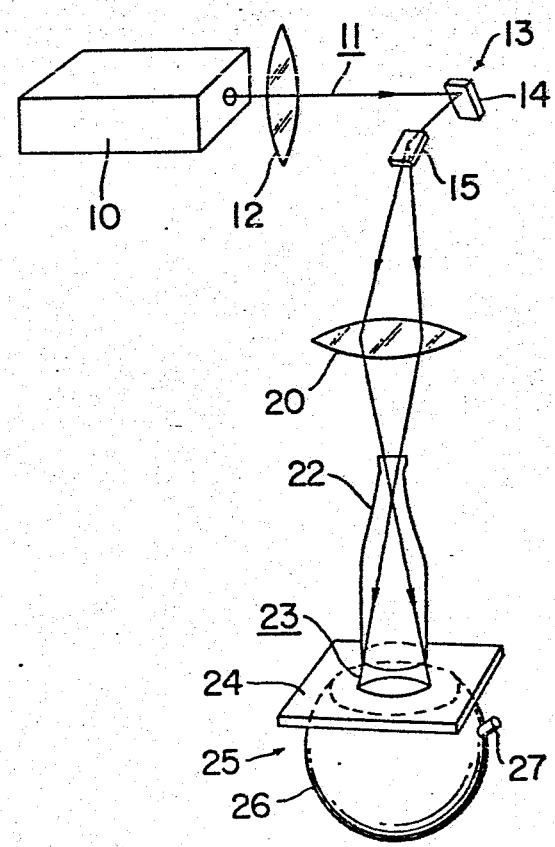
FIG. 1 is a schematic representation of a preferred form of the flaw detecting system in accordance with this invention.

The present invention is shown embodied, first of all, in the bottle flaw detecting system of FIG. 1, which includes a laser unit or a laser 10 such as that of the helium-neon or carbon dioxide variety. A converging lens 12 is positioned adjacent to the laser 10, across the path of the laser beam 11 emitted thereby, for collimating the same. The collimated laser beam falls upon an oscillatory mirror system 13 which functions to impart an annular or spiral scanning motion to the beam.

The oscillatory mirror system 13 comprises first 14 and second 15 reflecting mirrors. The first mirror 14 is arranged to directly receive the collimated laser beam 11 and is angled with respect to the beam axis. The second mirror 15 is arranged to reflect the laser beam 11 that has been reflected from the first mirror 14, and is likewise angled with respect to the incident beam axis.

Figure 2:
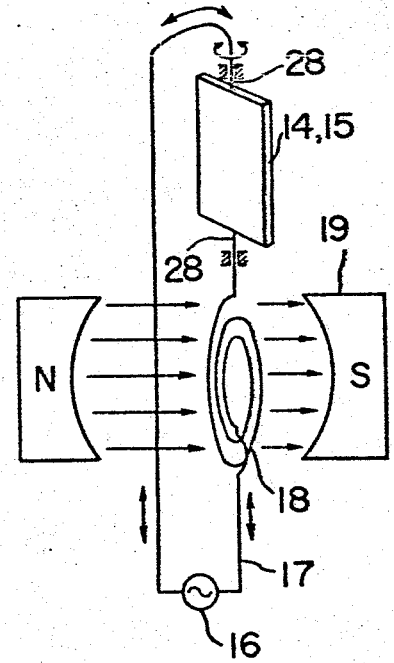
FIG. 2 is a schematic representation explanatory of means for oscillating each mirror of an oscillatory mirror system employed in the flaw detecting system of FIG. 1 to impart an annular or spiral scanning motion to the laser beam.

As better shown in FIG. 2, each of the mirrors 14 and 15 of the oscillatory mirror system 13 is pivoted by a pair of trunnions 28 affixed collinearly to its metal base, for oscillation thereon. The trunnions 28 of each oscillatory mirror 14, 15 are electrically connected to an alternating current (AC) source 16 to form a closed electric circuit 17. This closed circuit includes a coil winding 18 connected directly to one of the mirror trunnions 28 and disposed in a magnetic field generated by a permanent magnet 19.

Thus, by sending out alternating currents 90 degrees out of phase with each other into the respective closed circuits 17 of the mirrors 14 and 15, these mirrors can be oscillated about the trunnions 28 by the coil winding 18 lying in the prepared magnetic fields, as dictated by Fleming's rule. The noted phase relationship of the alternating currents correlates the oscillations of the mirrors 14 and 15 so that they may coact to impart an annular scanning motion to the collimated laser beam 11 as the latter is reflected by the successive mirrors. A continuous change in the angles or amplitudes of oscillation of the mirrors 14 and 15 results in a continuous change in the diameter of the scanning loop of the laser beam as measured in any fixed plane. More will be said presently concerning this function of the oscillatory mirror system 13.

With reference back to FIG. 1, the collimated laser beam 11 that has received the annular scanning motion passes through another converging lens 20 into a bottle 22, such as a used and cleaned beer bottle, which is being held in a preassigned position to be tested as to the presence of flaws. The surface curvature of this converging lens 20, which is shown to be of the double convex type, and its distance from the bottle 22 are so determined that its focus may lie at the mouth of the bottle or thereabouts.

Thus the converging lens 20 serves to direct the scanning laser beam 11 into the bottle 22 through its mouth. By continuously varying the diameter of the scanning loop of the beam in any fixed plane, as noted previously, the beam will scan not only the inside surface of the bottom, but also that of the entire side wall, of the bottle 22.

A sheet of ground glass 24 is disposed across the path 23 of the scanning laser beam that has passed through the bottle 22, so as to be irradiated thereby. After thus irradiating the ground glass 24, the laser beam is directed onto photoelectric sensing means generally labelled 25. In this particular embodiment the photoelectric sensing means 25 comprises an integrating sphere 26 mounted immediately under the ground glass 24, with its inlet opening 26a held against the glass, and a photoelectric detector 27 mounted in the usual window of the integrating sphere.

Figure 3:
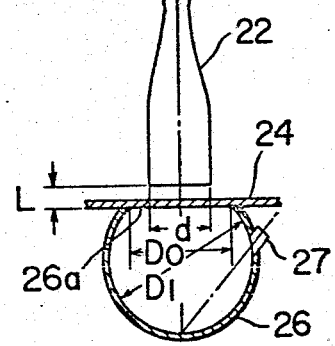
FIG. 3 is a sectional view of photoelectric sensing means in the system of FIG. 1, the view showing in particular the integrating sphere of the photoelectric sensing means in its correct positional relationship to the bottle being tested.

Attention is now called to the details of the photoelectric sensing means 25 given in FIG. 3. The photosensitive face of the photoelectric detector 27 is disposed flush with the inside surface of the integrating sphere 26 and, preferably, is oriented toward the bottom center of the sphere. Receiving the laser beam from the ground glass 24 through its inlet opening 26a, the integrating sphere 26 functions to reflect the incoming beam onto the photoelectric detector 27. The diameter $D_o$ of the integrating sphere opening 26a is made suitably greater than the diameter d of the bottle 22 in order that the laser beam that has scanned the bottle may enter the sphere.

Figure 4:
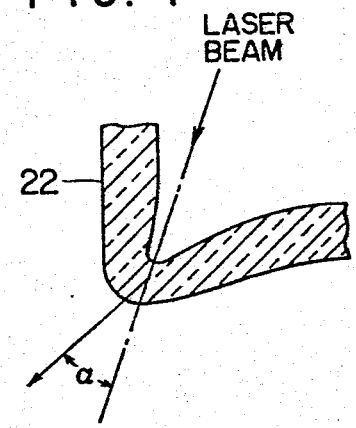
FIG. 4 is a fragmentary, enlarged vertical sectional view of the bottle being tested, the view being explanatory of the refraction of the scanning laser beam as the same passes through the perimeter of the bottom of the bottle.

Glass bottle making techniques today are such that the bottoms of bottles, particularly their peripheral regions, are often of uneven thickness. This, possibly combined with the refractive power of the bottom walls, may cause irregular diffusion or deflection of the scanning laser beam. In some instances, as depicted in FIG. 4, the laser beam scanning the perimeter of the bottle bottom may be refracted outwardly through an angle $\alpha$ of as much as 50 degrees from its straight-line path. The inlet opening 26a of the integrating sphere 26 should therefore be sufficiently large, in relation to the bottle diameter d and to the distance L between bottle and sphere, to receive all such outwardly refracted light.

Preferably, the diameter $D_o$ of the integrating sphere opening 26a is about 80% of the inside diameter $D_i$ of the sphere. This relative opening diameter is greater than that of ordinary integrating spheres available commercially. The integrating sphere 26 with such a large opening 26a can be reduced in its overall size without sacrifice of its ability to collect the laser beam. The use of such a small-size integrating sphere also contributes materially to the reduction of the installation space for the complete flaw detecting system and further to the ease of installation, supervision, and maintenance.

If it is assumed that the bottles to be tested have diameters of up to about 75 millimeters (mm), the integrating sphere 26 may have an inside diameter $D_i$ of 150 mm and an opening diameter $D_o$ of 120 mm. As is well known, the spherical inside surface of the integrating sphere 26 reflects the incident laser beam onto the photoelectric detector 27.

The photoelectric detector 27 exhibits a change in its output current amplitude when the incident radiation has been modulated by some flaw in the bottle 22. This change in the output of the photoelectric detector 27 serves as an indication of the presence of a flaw in the bottle being tested. More detailed explanation of this process of flaw detection follows.

If the bottom of the bottle 22 has some foreign matter sticking thereto, or has a scratch, crack or other defect formed therein, then the annularly or spirally scanning laser beam will undergo depolarized reflection on impinging on such faulty part of the bottle bottom. This of course results in a decrease in the intensity of the light entering the integrating sphere 26 through the ground glass 24. If some flaw lies in the side wall of the bottle 22, on the other hand, then the flaw will either intercept or polarizingly reflect the scanning laser beam. The result, again, is a decrease in the intensity of the light travelling into the integrating sphere 26. Since the total incident light of the integrating sphere 26 is thereby reflected onto the photoelectric detector 27, the latter senses the presence of a flaw in the bottle 22 from the reduction of the incident radiation.

Figure 5A:
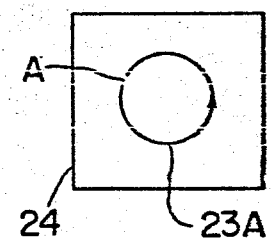
FIG. 5A is a plan view of a sheet of ground glass covering the inlet opening of the integrating sphere in the system of FIG. 1, the view further showing the path as traced on the ground glass by the laser beam during its single scanning cycle, the letter A in this view denoting the presence of a flaw in the bottle being tested.
Figure 5B:
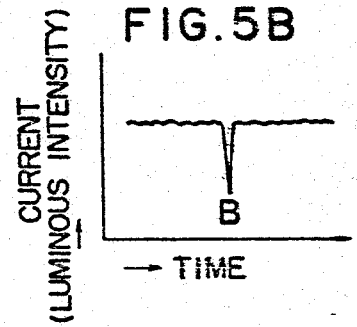
FIG. 5B graphically represents the intensity of the light falling, during the single scan of the laser beam as depicted in FIG. 5A, on the photodetector forming a part of the photoelectric sensing means in the system of FIG. 1, the letter B in this graph indicating a drop in the intensity of the incident light corresponding to the bottle flaw A in FIG. 5A.

A consideration of FIGS. 5A and 5B will further clarify the function of the photoelectric detector 27. FIG. 5A pictures the path of the scanning laser beam as traced on the ground glass 24 during its single annular or circular sweep of the bottle 22. The scanning beam has just encountered a flaw at A, which actually may be anywhere in the bottom or side wall of the bottle. At this faulty spot A the scanning beam has been either blocked or depolarized reflected, resulting in a corresponding change in the intensity of the light received by the integrating sphere 26 and therefore by the photoelectric detector 27.

The graph of FIG. 5B shows a curve of the corresponding incident radiation on the photoelectric detector 27, and therefore of its output current, against time. The bottle flaw at A, encountered by the scanning laser beam as described above, has caused a sudden drop at B in the incident radiation and hence in the output current of the photoelectric detector 27. This drop in the output current indicates the presence of the flaw in the bottle.

The following is a description of how the oscillatory mirror system 13 operates to impart the desired annular or spiral scanning motion to the converged laser beam 11. In the closed electric circuit of FIG. 2, including the coil winding 18 disposed in the magnetic field of the permanent magnet 19, the flow of an alternating current therethrough results in the exertion of forces on the coil winding in alternately reversed directions at right angles to the net directions of current flow through the coil winding and to the direction of the magnetic lines of force, in accordance with Fleming's left hand rule. Such forces cause oscillation of each mirror 14, 15 about the trunnions 28.

Figure 6:
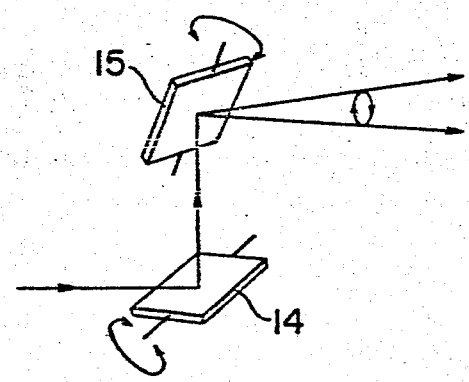
FIG. 6 is a perspective view explanatory of how the annular or spiral scanning motion is imparted to the laser beam by the oscillatory mirror system used in the flaw detecting system of FIG. 1.
Figure 7A:
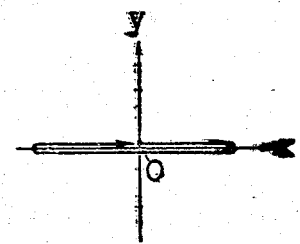
FIGS. 7A and 7B are graphic representations of the operating principle of the oscillatory mirror system of FIG. 6.

As clearly shown in FIG. 6, the first 14 and the second 15 mirrors of the oscillatory mirror system 13 are disposed with their axes of oscillation in right angular relationship to each other. Further, the alternating currents driving the two mirrors 14 and 15 have a phase difference of 90 degrees. If the first mirror 14 is oscillated as described above to cause the swinging motion x of the laser beam along the X-axis, as shown in FIG. 7A, then $$x = a \sin w t \qquad (1)$$

where a is a constant proportional to the magnitude of the alternating current driving each mirror; w is the angular velocity ($= 2\pi f$); and t is the time.

Figure 7B:
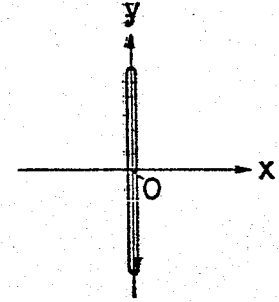

The second mirror 15 oscillates to cause the swinging motion y of the laser beam along the Y-axis as in FIG. 7B. Since the alternating current driving this second mirror 15 is 90 degrees out of phase with that driving the first mirror, $$y = a \sin (w t - \pi/2) = a \cos w t \qquad (2)$$

The laser beam 11 is reflected successively by these oscillating mirrors 14 and 15. Hence, from equations (1) and (2), $$x^2 + y^2 = a^2 \qquad (3)$$

The two oscillatory mirrors 14 and 15 thus coact to impart the desired annular scanning motion to the laser beam 11. A continuous change in the magnitude of the alternating currents driving the mirrors 14 and 15 affords a spiral scanning motion, with the diameter of the scanning loop of the laser beam in any fixed plane changing continuously. As required, moreover, the mirrors 14 and 15 may be oscillated with the magnitudes of the driving currents held at a prescribed ratio, to cause the laser beam to follow an elliptic scanning path.

The oscillatory mirror system 13 thus enables the laser beam 11 to scan, point by point, the bottom and side wall of a bottle or the like of almost any shape or size. Furthermore, since the scanning laser beam has been collimated by the converging lens 12, any flaw in the bottle being tested causes a very substantial change in the intensity of the light falling on the photoelectric detector 27. The invention thus succeeds in providing a highly reliable flaw detecting system.

Figure 8:
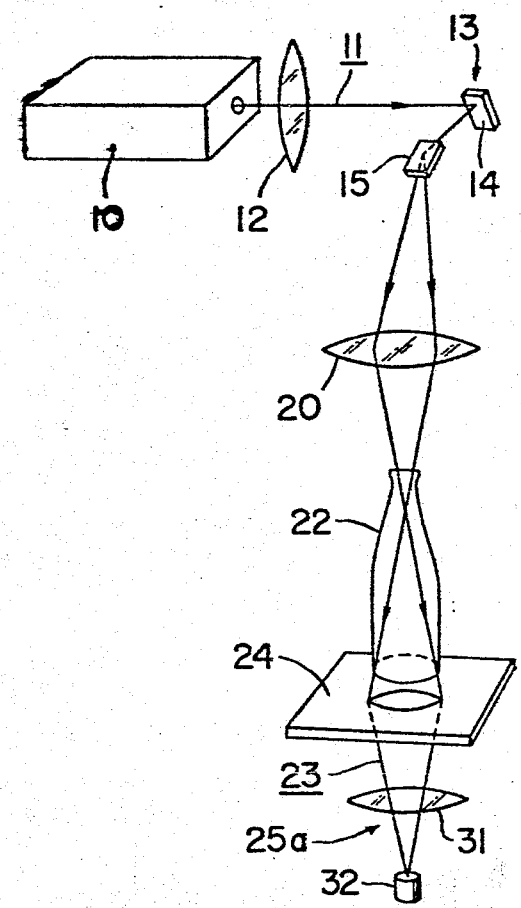
FIG. 8 is a schematic representation of another preferred form of the flaw detecting system in accordance with the invention.

FIG. 8 illustrates another preferred embodiment of this invention, which differs from the system of FIG. 1 only in its photoelectric sensing means. The other parts or components of this modified system are identified in FIG. 8 by the same reference numerals as those used to denote the corresponding parts of the FIG. 1 system, and their description will be omitted.

The modified photoelectric sensing means, generally designated by 25a in FIG. 8, comprises a converging lens 31 disposed next to the sheet of ground glass 24, and a photoelectric detector 32 disposed at the focal point of the converging lens 31 away from the ground glass. The converging lens 31 serves to direct on the photoelectric detector 32 the laser beam that has scanned the bottle 22 and which has further passed through the ground glass 24. Continuously receiving the scanning laser beam directed thereon, the photoelectric detector 32 senses any flaw in the bottle 22 from the intensity of the incident beam. The other details of construction and operation will be apparent from the foregoing.

Figure 9:
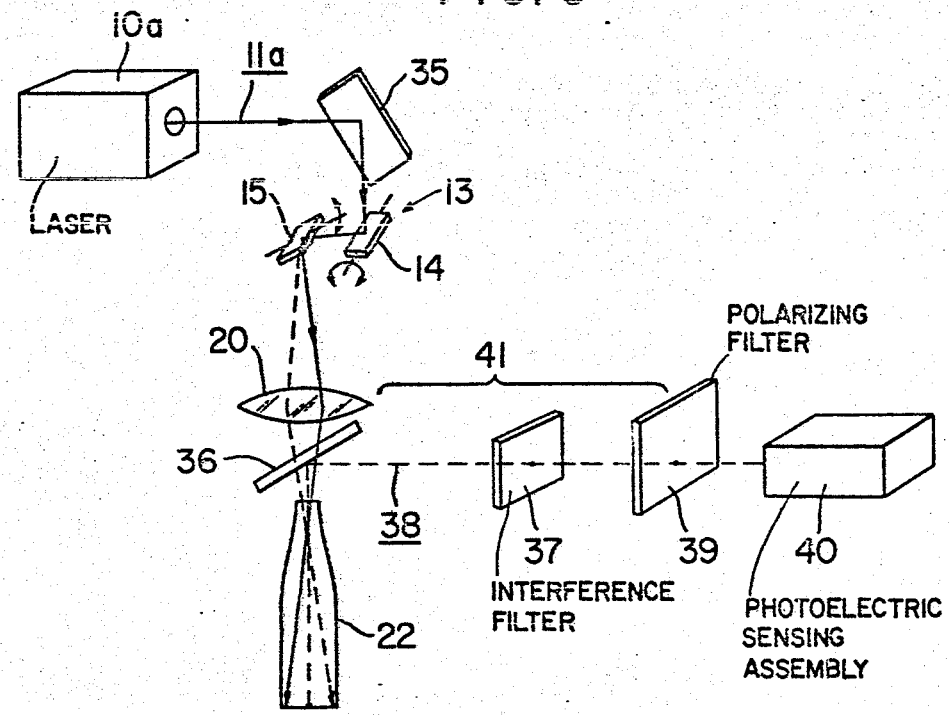
FIG. 9 is a schematic representation of still another preferred form of the flaw detecting system in accordance with the invention.

According to still another preferred embodiment of the invention shown in FIG. 9, any flaw in a bottle or other article is detected from the depolarized rays of the scanning laser beam that have been reflected from the flaw in the bottle. In this respect, the system of FIG. 9 contrasts with the two preceding embodiments of the invention which both rely for flaw detection on the intensity of the laser beam that has passed through the test article. Some parts or components of this FIG. 9 system also have their counterparts in the systems of FIGS. 1 and 8. Such corresponding parts are identified by like reference characters and will not be described in any detail.

A helium-neon or carbon dioxide laser 10a incorporated in the system shown in FIG. 9 includes Brewster windows at opposite ends of its discharge tube (not shown), so that its output beam 11a is linearly polarized (or plane-polarized), with its polarization plane kept constant. The construction of this laser 10a is known and by itself forms no novel feature of this invention.

The converging lens 12 of the preceding embodiments of the invention is not used here; instead, a totally reflecting mirror is disposed at 35 at an angle to the axis of the linearly polarized beam 11a being generated by the laser 10a. The mirror 35 reflects and redirects the laser beam 11a onto the oscillatory mirror system 13 comprising the first 14 and the second 15 oscillatory mirrors.

The oscillatory mirror system 13 functions as above explained to impart an annular or spiral scanning motion to the laser beam 11a. The laser beam subsequently reaches the converging lens 20, which directs the beam at or adjacent the mouth of the bottle 22 being tested. How the laser beam scans the bottle 22 is clear from the foregoing description of the system shown in FIG. 1, in particular.

Included in means 41 (FIG. 9) for deriving from the reflected laser beam the depolarized rays that have been scattered by some flaw in the bottle 22, a beam splitter (half mirror) 36 is disposed between converging lens 20 and bottle 22 and functions to separate the reflected beam from the incident light. Of course, the beam splitter 36 transmits the incident scanning laser beam and reflects the light 38 that has been reflected back from the inside surfaces of the bottle 22. The deriving means 41 further comprises an interference filter 37 and a polarizing filter 39.

The interference filter 37 is arranged to directly receive the reflected light 38 from the beam splitter 36. The function of this interference filter is to permit the passage therethrough of only a preselected wavelength (e.g., 5328 angstroms (A) in the case of the He-Ne gas laser beam) of the incoming light and to filter out all other wavelengths by interference phenomenon. The particular wavelength of the reflected laser beam that has passed the interference filter 37 subsequently falls on the polarizing filter 39.

Figure 10:
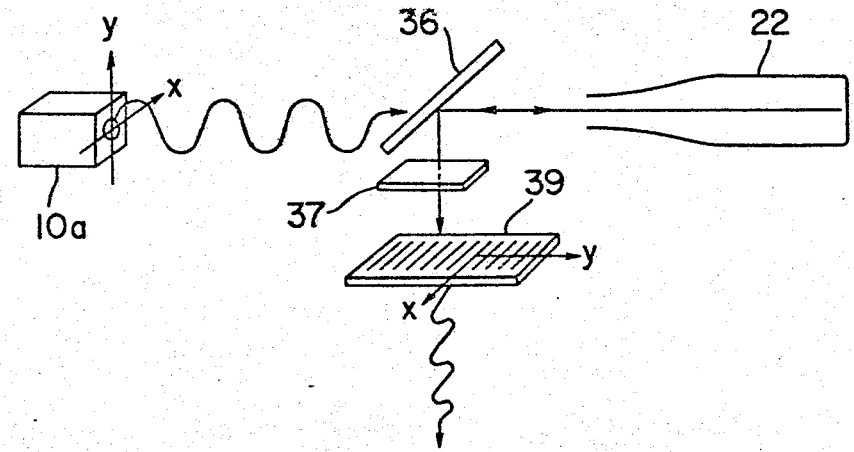
FIG. 10 is also a schematic representation explanatory of the operating principle of the flaw detecting system of FIG. 9.

For a better understanding of the function of the polarizing filter 39, reference is directed to the explanatory representation of this flaw detecting system in FIG. 10. If the laser beam 11a as generated by the laser 10a is linearly polarized in the y direction, for example, then the polarizing filter 39 is preadjusted to pass the incoming light polarized in the x direction only and to filter out that which is polarized in the y direction. Thus, provided that the bottle 22 has no flaw therein, the polarizing filter 39 blocks all the incoming light that has been reflected from the inside surfaces of the flawless bottle.

In the event that the bottle 22 has some flaw therein, however, the laser beam on scanning the flaw will undergo depolarized reflection, thereby creating components polarized in the x direction. The polarizing filter 39 passes such components of the depolarizingly reflected rays onto a photoelectric sensing assembly 40. Thus irradiated, a photoelectric detector (not shown) built into this assembly 40 senses the presence of the flaw in the bottle 22.

One of the features of the system shown in FIG. 9 resides in the interference filter 37. Since this filter blocks all but the reflected laser beam, the system permits accurate detection of any flaw in the bottle even in bright ambient light. This system is further capable of detecting any such transparent material as cellophane that may be attached to the bottle, because the laser beam is reflected even by such transparent material. An additional, but no less important, advantage of this system is that it finds use not only with glass bottles but also with cans or other open-ended containers of nontransparent material. It will of course be seen that the beam splitter or half mirror 35 of FIG. 9 can be replaced by a reflecting mirror having an aperture formed centrally therein or by an optical glass fiber.

Figure 11:
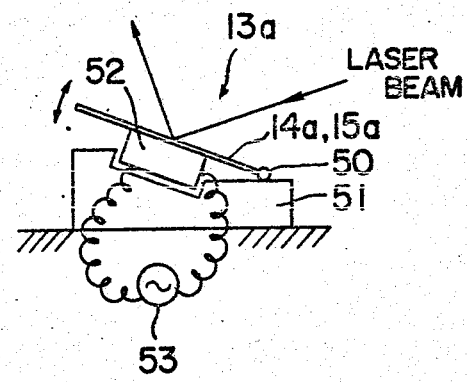
FIG. 11 is a schematic side view of a modification of the oscillatory mirror system used in the flaw detecting systems of FIGS. 1, 8 and 9, the view showing only one of the required two mirrors together with means directly associated therewith.

A variety of modifications are possible for the oscillatory mirror system 13 which has been described with particular reference to FIGS. 2, 6 and 7 and which has been incorporated in all the three preceding embodiments of the invention illustrated in FIGS. 1, 8 and 9. FIG. 11 schematically illustrates one of such possible modifications. The modified oscillatory mirror system 13a also employs two mirrors 14a and 15a arranged just like the mirrors 14 and 15 of the original system 13. The modification resides in the means for imparting oscillations to the two mirrors. Since the two mirrors are oscillated by identical means, only one of the mirrors will be shown and described in connection with its own oscillatory means.

FIG. 11 shows the representative mirror 14a, 15a as being pivotally supported along one edge 50 on a support 51. At or adjacent its free edge the mirror 14a, 15a rests upon a piezoelectric crystal unit 52 recessed into the support 51 and electrically connected to an AC source 53. Of the type available commercially, the piezoelectric crystal unit 52 includes a piezoelectric crystal element which vibrates at a desired frequency when placed in an electric circuit as in the illustrated arrangement.

Thus, upon application of alternating current to the piezoelectric crystal unit 52 from the AC source 53, the crystal element generates mechanical vibrations at the frequency of the alternating current. The amplitude of the alternating current determines the amplitude of the crystal vibrations. The piezoelectric crystal unit 52 thus oscillates the mirror 14a, 15a at a desired frequency and with a desired amplitude.

The other, unshown mirror of the modified mirror system 13a is likewise oscillated at a desired frequency and with a desired amplitude. With their oscillations properly correlated, the two mirrors 14a and 15a of the modified mirror system coact to impart an annular or spiral scanning motion to the laser beam by successively reflecting the same. For a more extensive discussion of the method of thus imparting the annular or spiral scanning motion to the laser beam, reference is directed to the description of FIGS. 6, 7A and 7B and, by way of comparison, to that of FIG. 2.

Figure 12:
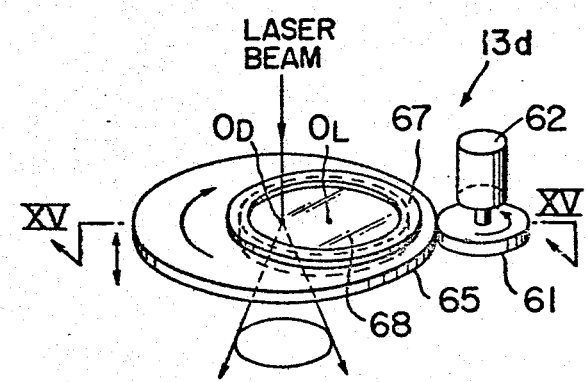
FIG. 12 is a perspective view of second modified means for imparting an annular or spiral scanning motion to the laser beam in the system of either FIG. 1, 8 or 9.
Figure 13:
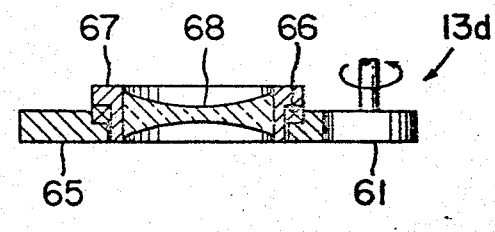
FIG. 13 is a sectional view of the means of FIG. 12, taken along the plane indicated at XIII—XIII in that figure.

FIGS. 12 and 13 illustrate still another modification of the oscillatory mirror system 13, in which a lens holder 67 in the form of a hollow, flanged cylinder immovably holds a lens 68, which is shown as a double concave one. The lens holder 67 together with the lens 68 is rotatably mounted via a bearing 66 in a hole formed eccentrically in a disclike lens carrier 60. This lens carrier 60 is also to be rotated by the motor 62 via the drive roll or disc 61. The axis $O_L$ of the lens 68 is offset from the axis $O_D$ of the lens carrier 60, and the radius of the lens 68 is greater than the distance between lens axis $O_L$ and lens carrier axis $O_D$. Thus, as the incident laser beam falls on the lens 68 on the axis $O_D$ of the lens carrier 60, the lens 68 revolving around the lens carrier 68 imparts the desired annular scanning motion to the laser beam passing therethrough. Gradual axial movement of the lens carrier 60 results in a continuous change in the diameter of the scanning circle of the laser beam in any fixed plane.

One of the most pronounced features in the operation of the arrangement 13d of FIGS. 12 and 13 is that during the rotation of the lens carrier 65 about its own axis $O_D$, the lens 68 together with its holder 67 is locked against angular displacement about its own axis $O_L$ by suitable means (not shown). Although the lens 68 revolves about the lens carrier axis $O_D$, its angular position about its own axis $O_L$ remains unchanged during the rotation of the lens carrier 65. Falling on the revolving lens 68 at the lens carrier axis $O_D$, therefore, the incident laser beam follows a circular path on the lens in passing therethrough to receive the desired annular scanning motion therefrom.

The combined rotary and axial movements of the lens carrier 65 give a spiral scanning motion to the laser beam. A rack-and-pinion mechanism, fluid actuated cylinder, or any other suitable means may be employed to effect such axial movement of the lens carrier 65. Of course, a converging lens could be used in place of the diverging lens 68, and gearing and other drives could be substituted for the friction drive used in the arrangement of FIGS. 12 and 13. Furthermore, as desired, light beams other than a laser beam may be adopted in the practice of this invention.

The above and various other modifications or changes that will readily occur to those versed in the art are intended in the foregoing disclosure. It is therefore appropriate that the present invention be construed broadly.

What is claimed is:

1. In a system for detecting flaws in bottles or like articles having a neck or constricted area near the top thereof, said system including a light beam generating means, a device for causing scanning motion of said light beam through an article to be tested, and a photoelectric detecting means adapted for detecting variation of said scanned light beam thereby to detect a flaw in the article the improvement wherein said system comprises: a laser beam generating means for generating a narrow beam of light; mirror means comprising two mirrors having respective reflective surfaces arranged so as to reflect said laser beam one after the other and supported so as to be oscillated about respective axes at right angles to each other and lying in respective planes which substantially coincide with the respective reflective surfaces for generating a scanning motion of the laser beam; means for imparting correlated oscillations to said two mirrors whereby the beam is angularly scanned in a spiral path; a positive lens for receiving said scanned beam and for redirecting it through a cross-over point or small region positioned within said bottle or article at said neck or constricted area; and, a photoelectric detector means adapted for receiving said spirally scanned laser beam after it has passed through or been reflected by said article thereby to detect a flaw in the article to be tested.

2. The improved system of claim 1 wherein each mirror is planar and is provided with a pair of trunnions defining the axis of oscillation of the mirror and the means for imparting said correlated oscillations to the two mirrors comprises: two closed electric circuits connected respectively to each mirror, each of said circuits including a coil part connected integrally to the respective mirror through the trunnions thereof and disposed in respective magnetic fields means for passing alternating current through each of said closed circuits, said alternating currents being 90 degrees out of phase with each other to cause correlated oscillations of the mirrors.

3. The improved system of claim 1 in which: each of the two mirrors is planar and is pivotally supported at one edge on a support; the means for imparting correlated oscillations to the mirrors comprises piezoelectric units, each attached to a respective one of the two mirrors and rested in a recess of said support, and means for passing alternating current through each of said piezoelectric units, said alternating currents being 90 degrees out of phase with each other.

4. The improved system of claim 1 wherein there is further provided a converging lens disposed between the mirror means and the article lying in a preassigned position to be tested as to the presence of flaws, said converging lens being adapted to direct the laser beam into the article by directing the laser beam at a point adjacent the mouth of the article thereby to cause scanning motion of the laser beam through the bottom and side wall of the article; and, wherein the photoelectric detecting means for receiving the scanned laser beam and sensing a flaw in the article is positioned where the laser beam, having been scanned through the article, is directed.

5. A flaw detecting system according to claim 4, further comprising another converging lens disposed between the laser and the optical means for collimating the laser beam.

6. A flaw detecting system according to claim 4, wherein the system further comprises a sheet of ground glass disposed between the bottle and the receiving and sensing means.

7. In a system for detecting flaws in bottles or like articles having a light beam generating means, a device for causing scanning motion of said light beam through an article to be tested, and a photoelectric detecting means adapted for detecting variation of said scanned light beam thereby to detect a flaw in the article, the improvements wherein said light beam generating means is a laser and wherein said device for causing a scanning motion includes: a lens carrier arranged for rotation about the axis of the laser beam; a lens rotatably carried by said lens carrier in an eccentric position thereon and having a radius greater than the distance between its own axis and the axis of the laser beam; means for rotating the lens carrier about the axis of the laser beam, the lens being locked against angular displacement about its own axis during the rotation of the lens carrier.

8. In a system for detecting flaws in bottles or like articles having a light beam generating means, a device for causing scanning motion of said light beam through an article to be tested, and a photoelectric detecting means adapted for detecting variation of said scanned light beam thereby to detect a flaw in the article the improvements wherein: (a) said light beam generating means is a laser beam generating means adapted to generate a narrow linearly-polarized laser beam; (b) said device for causing scanning motion comprises optical means disposed in the path of said polarized laser beam and adapted to move in a prescribed manner for imparting angular deflections to said beam to cause it to undergo an annular or spiral scanning motion and a positive lens for receiving said scanned laser beam and for redirecting it through a cross-over point or a small region positioned within said bottle or article and above the surface to be inspected to thereby enable said beam to scan through said article; and, (c) said photoelectric detecting means comprises means for receiving light of said laser beam which is reflected from the article, the reflected light including depolarized rays produced as a result of scattering of the polarized laser beam by a flaw of the article, means for separating the depolarized rays from the reflected light, and means for sensing the presence of the flaw in the article by receiving only the separated depolarized rays.

9. A system for detecting flaws in bottles or like articles, as claimed in claim 8, wherein the receiving and separating means comprises: deflecting means disposed between the optical means and the article for deflecting the light reflected from the article, said deflecting means passing the polarized laser beam travelling from the optical means toward the article; an interference filter for passing therethrough only the light that has been deflected by said deflecting means; and, a polarizing filter for passing only the depolarized rays that have passed the interference filter.

10. A system for detecting flaws in bottles or like articles, as claimed in claim 8, wherein a converging lens is disposed between the optical means and the article for directing the polarized laser beam at a point adjacent the open end of the article.

* * * * *